(12) United States Patent
AbuAli et al.

(10) Patent No.: US 10,280,747 B2
(45) Date of Patent: May 7, 2019

(54) SAMPLING TECHNIQUES TO DETECT HYDROCARBON SEEPAGE

(71) Applicant: Saudi Arabian Oil Company, Dhahran (SA)

(72) Inventors: Mahdi AbuAli, Dhahran (SA); Maher I. Almarhoon, Qateef (SA); Khaled Arouri, Dhahran (SA)

(73) Assignee: Saudi Arabian Oil Company (SA)

( * ) Notice: Subject to any disclaimer, the term of this patent is extended or adjusted under 35 U.S.C. 154(b) by 232 days.

(21) Appl. No.: 15/158,290

(22) Filed: May 18, 2016

(65) Prior Publication Data

US 2016/0341038 A1    Nov. 24, 2016

Related U.S. Application Data

(60) Provisional application No. 62/164,277, filed on May 20, 2015.

(51) Int. Cl.

| | |
|---|---|
| *G01N 1/02* | (2006.01) |
| *G01N 1/08* | (2006.01) |
| *G01N 1/22* | (2006.01) |
| *G01V 9/00* | (2006.01) |
| *E21B 47/10* | (2012.01) |
| *E21B 49/08* | (2006.01) |
| *G01N 33/24* | (2006.01) |

(52) U.S. Cl.
CPC .............. *E21B 49/08* (2013.01); *E21B 47/10* (2013.01); *G01N 1/2294* (2013.01); *G01V 9/007* (2013.01); *G01N 1/08* (2013.01); *G01N 33/241* (2013.01); *G01N 2001/021* (2013.01)

(58) Field of Classification Search
CPC ........ E21B 49/08; G01N 1/08; G01N 1/2294; G01N 2001/021; G01N 33/241; G01V 9/007
See application file for complete search history.

(56) References Cited

U.S. PATENT DOCUMENTS

| | | |
|---|---|---|
| 2,305,384 A | 12/1942 | Hoover, Jr. |
| 5,010,776 A | 4/1991 | Lucero et al. |
| | (Continued) | |

FOREIGN PATENT DOCUMENTS

WO    2013/071185    5/2013

OTHER PUBLICATIONS

Matthews, "Importance of Sampling Design and Density in Target Recognition", AAPG Memoir 66, pp. 243-253.

(Continued)

*Primary Examiner* — Randy W Gibson
*Assistant Examiner* — Gedeon M Kidanu
(74) *Attorney, Agent, or Firm* — Fish & Richardson P.C.

(57) ABSTRACT

Methods, systems, and apparatus, including computer programs encoded on a computer storage medium, for detecting seepage of hydrocarbons in subterranean zones. In one aspect, a method includes detecting hydrocarbon seepage at multiple different sampling depths from a surface in a surveyed geographic region, comparing each of the hydrocarbon seepage at the multiple different sampling depths, wherein hydrocarbon seepage at a reference depth is known, and determining hydrocarbon seepage through the surveyed geographic region based on a result of the comparison.

16 Claims, 2 Drawing Sheets

(56) References Cited

U.S. PATENT DOCUMENTS

| | | | | |
|---|---|---|---|---|
| 5,410,252 | A * | 4/1995 | Potter | G01V 3/087 |
| | | | | 324/345 |
| 2010/0286967 | A1 * | 11/2010 | Vasilevskiy | G01V 7/00 |
| | | | | 703/2 |
| 2013/0301672 | A1 * | 11/2013 | Tonina | G01K 13/02 |
| | | | | 374/45 |
| 2013/0327125 | A1 * | 12/2013 | He | G01N 1/08 |
| | | | | 73/31.05 |

OTHER PUBLICATIONS

PTTC Technology Connections, "Surface Hydrocarbon Detection Shows Promise", Published on or before Feb. 1999, 2 pages.

Fontana et al., "Past, Present and Future Advancements in Methods for Detecting Hydrocarbon Seepage after 75 Years", copyright 2014, 49 pages.

Van Der Meer et al., "Hyperspectral Hydrocarbon Microseepage Detection and Monitoring: Potentials and Limitations", published in 2000, 9 pages.

Schumacher, D. and M.A. Abrams, eds., 1996, "Hydrocarbon Migration and Its Near-Surface Expression," AAPG Memoir, 66, pp. 445.

Klusman, R.W., 1993, "Soil gas and related methods for natural resource exploration," New York, John Wiley & Sons, pp. 483.

International Search Report and Written Opinion issued in International Application No. PCT/US2016/033101 dated Aug. 4, 2016, 14 pages.

* cited by examiner

SAMPLING TECHNIQUES TO DETECT HYDROCARBON SEEPAGE

TECHNICAL FIELD

This specification relates to detection of seepage of hydrocarbons from subterranean zones.

BACKGROUND

Hydrocarbons, such as oil and gas, can be geochemically detected from particular subterranean zones. The identification of subterranean zones including hydrocarbon accumulations is becoming increasingly difficult to locate and access, as the demand for energy grows globally. In the past, drilling was often performed near to a visible oil seep (macroseep) to access hydrocarbon accumulations. Presently, macroseeps are relatively rare and efforts directed towards identification of hydrocarbon accumulations are mostly focused on detection of invisible oil seeps (microseeps). Various geochemical methods can be utilized for near surface exploration to measure data associated with microseeps. For example, sensitive instrumentation can be used for direct and indirect microseep detection methods. Improvements in technology and sensitivity of microseep detection methods may be beneficial in lowering the risk of hydrocarbon exploration and efficiently locating subsurface hydrocarbon accumulations.

SUMMARY

This specification describes geochemical methods relating to detection of seepage of hydrocarbons from subterranean zones.

In some examples, a method of sampling a geographic region for hydrocarbon seepage includes detecting hydrocarbon seepage at a first sampling depth from a surface in a surveyed geographic region, detecting hydrocarbon seepage at a second sampling depth from the surface, the second sampling depth deeper than the first sampling depth, detecting hydrocarbon seepage at a third sampling depth from the surface, the third sampling depth deeper than the second sampling depth, comparing each of the hydrocarbon seepage at the first sampling depth, the hydrocarbon seepage at the second sampling depth, and the hydrocarbon seepage at the third sampling depth with hydrocarbon seepage at a reference depth deeper than the first, second and third sampling depths, wherein hydrocarbon seepage at the reference depth is known, and determining hydrocarbon seepage through the surveyed geographic region based on a result of comparing each of the hydrocarbon seepage at the first sampling depth, the hydrocarbon seepage at the second sampling depth, and the hydrocarbon seepage at the third sampling depth with the hydrocarbon seepage at the reference depth.

In some implementations, detecting hydrocarbon seepage at the first sampling depth includes, detecting hydrocarbon seepage at the second sampling depth and detecting hydrocarbon seepage at the third sampling depth includes: positioning a first plurality of hydrocarbon sensors at the first sampling depth, positioning a second plurality of hydrocarbon sensors at the second sampling depth, and positioning a third plurality of hydrocarbon sensors at the third sampling depth, wherein the first plurality of hydrocarbon sensors, the second plurality of hydrocarbon sensors and the third plurality of hydrocarbon sensors are configured to detect hydrocarbons at the first sampling depth, the second sampling depth and the third sampling depth, respectively.

In some implementations, detecting hydrocarbon seepage at the first sampling depth includes, detecting hydrocarbon seepage at the second sampling depth and detecting hydrocarbon seepage at the third sampling depth includes: positioning a first plurality of hydrocarbon sensors at the first sampling depth, positioning a second plurality of hydrocarbon sensors at the second sampling depth, and positioning a third plurality of hydrocarbon sensors at the third sampling depth, wherein the first plurality of hydrocarbon sensors, the second plurality of hydrocarbon sensors and the third plurality of hydrocarbon sensors are configured to detect hydrocarbons at the first sampling depth, the second sampling depth and the third sampling depth, respectively.

In some implementations, positioning the first plurality of hydrocarbon sensors at the first sampling depth includes positioning the first plurality of hydrocarbon sensors in a two-dimensional array at the first sampling depth. The first sampling depth can be about 1.0 meter from the surface.

In some implementations, positioning the second plurality of hydrocarbon sensors at the second sampling depth includes positioning the second plurality of hydrocarbon sensors in a two-dimensional array at the second sampling depth. The second sampling depth can be about 5.0 meter from the surface.

In some implementations, positioning the third plurality of hydrocarbon sensors at the third sampling depth includes positioning the third plurality of hydrocarbon sensors in a two-dimensional array at the third sampling depth. The third sampling depth can be greater than 5.0 meter from the surface.

In some implementations, the method further includes positioning a reference hydrocarbon sensor at the reference depth, the reference hydrocarbon sensor configured to detect hydrocarbons at the reference depth. The reference depth can be within a hydrocarbon reservoir in the surveyed geographic region.

In some implementations, comparing each of the hydrocarbon seepage at the first sampling depth, the hydrocarbon seepage at the second sampling depth, and the hydrocarbon seepage at the third sampling depth with hydrocarbon seepage at a reference depth deeper than the first, second and third sampling depths includes detecting hydrocarbon seepage at the reference depth.

In some implementations, comparing each of the hydrocarbon seepage at the first sampling depth, the hydrocarbon seepage at the second sampling depth, and the hydrocarbon seepage at the third sampling depth with hydrocarbon seepage at a reference depth deeper than the first, second and third sampling depths includes: determining a reference hydrocarbon seepage signal that represents the hydrocarbon seepage at the reference depth, determining a first hydrocarbon seepage signal that represents the hydrocarbon seepage at the first sampling depth, determining a second hydrocarbon seepage signal that represents the hydrocarbon seepage at the second sampling depth, determining a third hydrocarbon seepage signal that represents the hydrocarbon seepage at the third sampling depth, subtracting the first hydrocarbon seepage signal from the reference hydrocarbon seepage signal, subtracting the second hydrocarbon seepage signal from the reference hydrocarbon seepage signal, and subtracting the third hydrocarbon seepage signal from the reference hydrocarbon seepage signal.

In some implementations, the hydrocarbon seepage at the first sampling depth, the hydrocarbon seepage at the second sampling depth and the hydrocarbon seepage at the third sampling depth can be detected at a first time instant and the method further includes: detecting, at a second time instant after the first time instant, hydrocarbon seepage at the first sampling depth, detecting, at the second time instant, hydrocarbon seepage at a second sampling depth from the surface, the second sampling depth deeper than the first sampling depth, detecting, at the second time instant, hydrocarbon seepage at a third sampling depth from the surface, the third sampling depth deeper than the second sampling depth, and comparing each of the hydrocarbon seepage at the first sampling depth detected at the second time instant, the hydrocarbon seepage at the second sampling depth detected at the second time instant, and the hydrocarbon seepage at the third sampling depth detected at the second time instant with hydrocarbon seepage at the reference depth determined at the second time instant.

In some implementations, the method further includes determining hydrocarbon seepage through the surveyed geographic region as a function of time based on a result of the comparing at the first time instant and the comparing at the second time instant. The method can also further include analyzing, based on the hydrocarbon seepage the first sampling depth, the hydrocarbon seepage at the second sampling depth, and the hydrocarbon seepage at the third sampling depth, a relationship between polar compounds and non-polar compounds included in the hydrocarbon.

The present disclosure also provides another method that includes actions of in a surveyed geographic region, detecting hydrocarbon seepage at a plurality of depths from the surface, comparing the hydrocarbon seepage at the plurality of depths with known hydrocarbon seepage at a reference depth that is deeper than the plurality of depths, and determining hydrocarbon seepage through the surveyed geographic region based on comparing the hydrocarbon seepage at the plurality of depths with known hydrocarbon seepage at the reference depth.

In some implementations, detecting hydrocarbon seepage at the plurality of depths from the surface includes positioning a plurality of hydrocarbon sensors at each depth of the plurality of depths, each hydrocarbon sensor configured to detect hydrocarbons at the respective depth. The plurality of depths includes three depths. The three depths include depths about 1.0 meter from the surface, about 5.0 meter from the surface, and greater than 5.0 meter from the surface. At each depth, hydrocarbon seepage is detected at a plurality of locations.

In some implementations, detecting hydrocarbon seepage at a plurality of locations includes positioning a plurality of hydrocarbon sensors in a two-dimensional array at each depth. The reference depth is within the hydrocarbon reservoir.

In some implementations, the hydrocarbon seepage at the plurality of depths is detected at a first time instant, and the method further includes: in the surveyed geographic region, detecting, at a second time instant after the first time instant, hydrocarbon seepage at the plurality of depths from the surface, comparing the hydrocarbon seepage at the plurality of depths at the second time instant with known hydrocarbon seepage at the reference depth at the second time instant, and determining hydrocarbon seepage through the surveyed geographic region as a function of time based on a result of the comparing at the first time instant and the comparing at the second time instant.

In some implementations, the method includes analyzing, based on the hydrocarbon seepage at the plurality of depths, a relationship between polar compounds and non-polar compounds included in the hydrocarbon.

The present disclosure further provides another method that includes actions of inserting a plurality of gas sampling probes into a subterranean formation, such that each of the plurality of gas sampling probes is inserted at a location different than the rest, detecting, at a first time instant, with each of the plurality of gas sampling probes a first set of geochemical data associated to the respective locations, determining a first spatial map based on the first set of geochemical data, detecting, at a second time instant, with each of the plurality of gas sampling probes a second set of geochemical data associated to the respective locations, determining a second spatial map based on the second set of geochemical data, generating a spatio-temporal map based on the first spatial map and the second spatial map, and determining seepage of hydrocarbons based on processing the spatio-temporal map. The plurality of gas sampling probes includes at least three gas sampling probes. Each of the plurality of gas sampling probes includes a respective length different from the rest, such that each of the plurality of gas sampling probes is inserted at a respective depth in the subterranean formation. At least one of the pluralities of gas sampling probes includes a respective length that is larger than one meter. The first and second set of geochemical data includes biological and chemical sampling of one or more of fluids, gases, and sediments.

In some implementations, determining the first and second spatial map includes measuring molecular and isotopic signatures of non-hydrocarbon gases and hydrocarbons. In some implementations, processing the spatio-temporal map includes differentiating between active and passive seepage. Processing the spatio-temporal map can also include filtering seepage signals.

In some implementations, determining seepage of hydrocarbons further includes at least one of satellite, airborne, acoustic and seismic techniques. Determining seepage of hydrocarbons can also include determining depth, type, quality, volume and location of a subsurface hydrocarbon.

The present disclosure further provides a system to detect hydrocarbons, the system includes: a plurality of gas sampling probes configured to be inserted into a subterranean formation, such that each of the plurality of gas sampling probes is inserted at a location different than the rest, a plurality of gas collection and concentrating devices, each of the plurality of gas collection and concentrating devices being removably attached to the plurality of gas sampling probes and being configured to collect, at a first time instant, a first set of geochemical data associated to the respective locations and at a second time instant, a second set of geochemical data associated to the respective locations, and a processor configured to determine a spatio-temporal map based on the first set and the second of geochemical data and to determine seepage of hydrocarbons based on processing the spatio-temporal map. The system can further include a seismometer configured to detect seismic waves at the respective locations. The details of one or more implementations of the subject matter described in this specification are set forth in the accompanying drawings and the description below. Other features, aspects, and advantages of the subject matter will become apparent from the description, the drawings, and the claims.

DETAILED DESCRIPTION

Figure 1:
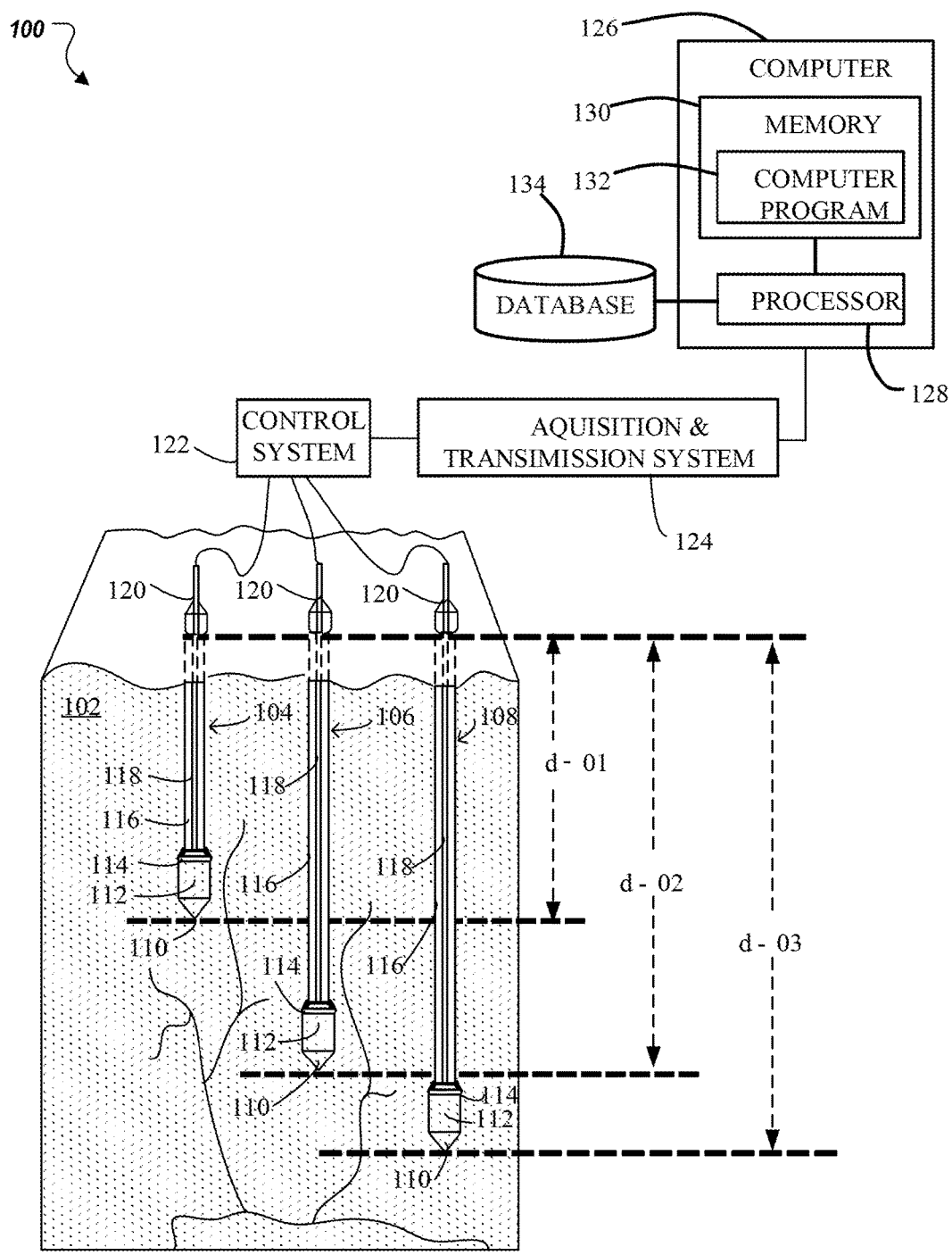
FIG. 1 illustrates an example of a multi-depth design for detecting seepage of hydrocarbons.

This specification relates to detection of hydrocarbon seepage and, in particular, hydrocarbon microseepage. The hydrocarbon present in subterranean zones can include oil, water, gas and solid (for example, rock deposits). A direct method to detect hydrocarbon seepage can include measuring reservoir hydrocarbons through soil-gas surveys. Surface prospecting technology offers an inexpensive tool to validate the presence of subsurface hydrocarbons ahead of the bit. Surface prospecting technology may reduce the overall exploration risk quite substantially if it can confirm the presence of hydrocarbons. Surface prospecting technology can also be used in prioritizing prospects and in inferring the nature of hydrocarbon accumulation (for example, oil versus gas). Surface prospecting technology can be used as an ancillary and integral component of other exploration tools to enhance their resolution.

Microseepage patterns are complex and can vary in space and over time. For example, in producing areas the gas concentration in overlying sediments increases. Reservoirs that are over-pressured presumably leak more intensely than under-pressured reservoirs. Active seepage leads to higher concentrations of hydrocarbons to the surface that may be easily detected by geochemical surveys. Fresh seepages may suggest an active generation and migration or, alternatively, leakage from an old accumulation induced by recent faulting/fracturing. Passive seepage can indicate a non-generating basin, resulting in weaker geochemical expressions at the surface, except in areas where major conduits are present such as faults. It is assumed that the geochemical expression at the surface primarily reflect the type of accumulation (oil versus gas), although the original composition and primary signal can be altered by other geological factors such as seal type, depth of accumulation and structural rejuvenation, among other factors. Knowledge of microseepage parameters including the concentration as a function of space and time can improve exploration success and open new potential areas.

Particular specifications of the detection method described can be implemented so as to realize one or more of the following advantages. The accuracy and reliability of the proposed method to detect the microseepage parameters is independent of the amount of gas void fraction. The multi-depth profiling method accounts for spatio-temporal variability and non-stationary nature of the signal. Any of the described method can be coupled with other subterranean exploration tools. The disclosed design engineered as a method to detect the microseepage parameters can be performed at off-shore or on-shore locations, such as in regions that were not previously explored for oil drilling or in regions including or near to old oil wells. The method characteristics allow for an enhancement of the seepage signal by measuring at multiple depths in the same test location and could, therefore, reduce the noise or contaminant (from a single measurement) by identifying new seepage-sensitive parameters. The result of this method is independent of all other remote sensing methods such as seismic, potential field and land sat images. It can also be integrated with other exploration methods such as seismic acquisition to simultaneously measure both the seepage concentration as well as the seismic reflection time through geophones. Such integration is critical in lowering the overall exploration risk.

As shown in FIG. 1, an example seepage detection system 100 can be implemented before well production to identify microseepage patterns in a subterranean formation 102. Measurement of microseepage patterns can help locate prospects and, eventually, support the optimization of well drilling and production. The example seep detection system 100 includes multiple gas sampling probes 104, 106, and 108 at multiple depths. The gas sampling probes 104, 106, and 108 can include a conventional post-run tubing gas sampling probe. In some implementations, the gas sampling probes 104, 106, and 108 can be inserted into the subterranean formation 102 by a "direct push" technique which involves the use of a hydraulically powered percussion machine to drive the tool into the ground without having to remove soil and make a path for the tool. In some implementations, a cordless rotary drill is used to drive the gas sampling probes 104, 106, and 108 can be inserted into the subterranean formation 102.

The gas sampling probes 104, 106, and 108 can include a tip 110, which can have a sharp end at the bottom and can be of a retractable or an expendable type. Attached to the tip 110 can be a slotted hollow tube 112 that has a plurality of vents or apertures through which gases emanating from the adjacent soil 102 may enter the hollow interior of the tube. A gas-conducting adapter 114 interconnects the hollow tube 112 with a rigid tubular driving shaft 116. The adapter 114 can include openings, such as vents and apertures, or the adapter 114 can be opened at the bottom to receive soil gases into the interior of the adapter. In some cases, depending upon the type of the soil and the subterranean depth selected to be studied, the hollow tube 112 can have different lengths, being configured to enable the insertion of the gas sampling probes 104, 106, and 108 at various depths.

The driving shaft 116 can be approximately the same length as the anticipated earth depth of the gas sampling probes 104, 106, and 108 when it is fully inserted (for example, 1.0 meter, 5 meters or 110 meters). The driving shaft 116 can conduct the hydraulic driving force to position the probe below the surface of the soil being tested. In some cases it is desirable to connect the tip 110 directly to the adapter 114. In such a case, after reaching the desired probe depth, the driving shaft 116 can be retracted to separate the tip 110 from the adapter 114, creating a vertical tunnel in the soil between the probe tip 110 and the vented bottom of the adapter 114, through which soil gases may flow to enter the adapter 114. In some implementations, the gas sampling probes 104, 106, and 108 include sorbers configured to absorb gas molecules. The gas sampling probes 104, 106, and 108 can be inserted in the soil and left in the soil for preset time intervals (for example, two weeks) that are sufficient to collect a significant quantity of soil gases that can be analyzed in the laboratory.

The soil gases that enter the interior of the adapter 114 can be conducted through the tubing 118 to a collecting and concentrating device 120, located at the surface. The collecting and concentrating device 120 can include a glass tube, or other suitable tubular materials. The collecting and concentrating device 120 can house a plurality of different granular materials packed in series within the tube, each of which acts as a molecular sieve for the different gases which may be of interest in determining the characteristics of a hydrocarbon deposit possibly positioned below the location at which the gas sampling probes 104, 106, and 108 was inserted into the subterranean formation 102. A molecular sieve is a material, whose surface pores are of such size as to admit the molecules of a certain gas which are then trapped within the material until released through a thermal or chemical process. By appropriate selection of the material, a particular gas may be trapped. The collecting and concentrating device 120 and the packed filtering materials therein can act to concentrate the light hydrocarbons found in the soil gas sample.

The tubing 118 can also be connected to a control device 122 that can assist the collection of gasses. In some implementations, the control device 122 is a timer that monitors the period during which the gas sampling probes 104, 106, and 108 are in the soil, collecting gas. In some implementations, the control device 122 is a vacuum/volume type of pump that is configured to actively draw the soil gases into the gas sampling probes 104, 106, and 108 and upwardly through the tubing 118. The vacuum/volume pump can be shut off after sampling is complete and the collecting and concentrating device 120 is disconnected from the tubing line 118 after the line pressure returns to ambient atmospheric pressure. The sample acquired by the gas sampling probes 104, 106, and 108 or the collecting and concentrating device 120 can be processed, for example at a lab to retrieve geochemical data. The geochemical data can be transmitted to an acquisition and transmission system 124.

The acquisition and transmission system 124 can include multiple parts, such as a data acquisition and transmission system unit, to perform functions, such as amplifying the signals if necessary, sampling and digitizing the analogue signals into digit format by the data acquisition unit, and transmission the digitized signals to the computer 126. The acquisition and transmission system 124 can include a processor assembly, two encoder/decoder systems, and a conventional geochemical telemetry system. The acquisition and transmission system 124 can include components that are located within the gas sampling probes 104, 106, and 108 and components that are located above the ground surface. The digitized geochemical signals, generated by the data acquisition and transmission system 124, are sent to the computer 126. The computer 126 can include various components such as, for example, an electronic processor 128, memory 130 contained within, carried by, or otherwise operably coupled with the electronic processor 128, and a hydrocarbon seepage analyzing program 132 stored therein, which can adapt the computer 126 to perform program functions. The digitized geochemical signals are read by the hydrocarbon seepage analyzing program memory 130 or in a database 134 accessible to the processor 128 of the computer 126. The hydrocarbon seepage analyzing program 132 analyzes the geochemical signals to derive a three-dimensional spatial map or a four-dimensional spatio-temporal map of geochemical concentrations measured at various locations over the survey area.

In some implementation, the acquisition and transmission system 124 further receives data associated to the investigated subterranean zone 102, from one or more other devices. For example, the acquisition and transmission system 124 can receive seismic data from a seismometer, magnetic data from a magnetometer or gravity data from a gravimeter seismic data. In some implementation, the example seepage detection system 100 can further include airborne and/or remote gas sensing techniques.

Figure 2:
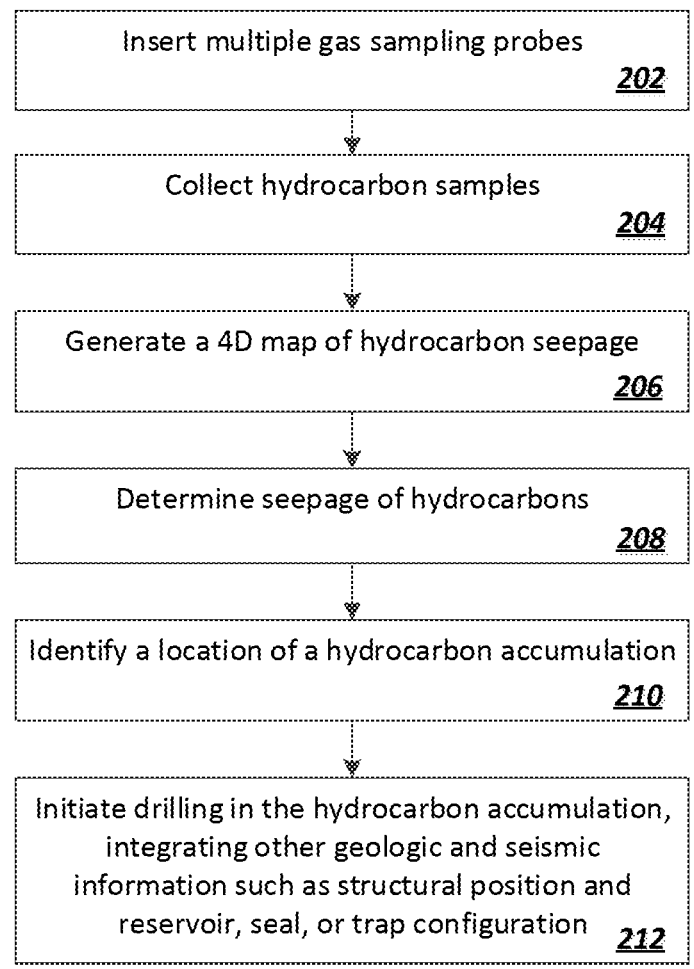
FIG. 2 is a flowchart of an example process for detecting seepage of hydrocarbons.

FIG. 2 is a flow chart showing an example process 200 for detection of hydrocarbon seepage. In some instances, the process 200 is used to assist the selection of a location for drilling. At 202, multiple (at least 3) gas sampling probes are inserted into the subterranean formation at different depths in different locations corresponding to particularly selected points in a surveying area. For example, the positions of the plurality of hydrocarbon sensors form a two-dimensional array at each depth. The depths, at which the gas sampling probes are inserted, can vary between 1.0 meters and 10 meters under the surface level. The locations, at which the gas sampling probes are inserted, can cover a surface of several square kilometers (for example, 100 square kilometers). The gas sampling probes can be inserted into the subterranean formation at particular distances (for example, 1 kilometer) apart from each other. The insertion location for the gas sampling probes can be selected based on soil conditions and the desired depth of the probe. The criterion for selecting the location of the gas sampling probes is based on a gridded survey targeting an area that is geologically prospective for hydrocarbon accumulations. The insertion locations and depths of the gas sampling probes can be selected based on a grid that supports or matches a particular statistical method of analyzing the hydrocarbon seepage. The gas sampling probes (for example, sorbers) are horizontally and vertically spaced at a selected distance from each other within a selected space and the gas absorbed by each gas sampling probe can be mapped out over the survey space. Results can identify areas of high gas concentrations within the survey space, presumably corresponding to hydrocarbon accumulations in the subsurface.

In some implementations, the gas sampling probes can be attached to the leading end of a hollow steel driving shaft which is advanced into the soil profile using a hydraulic hammer. The down-hole tools including the probe tool, the driving shaft and the hydraulic hammer can be conventional pieces of equipment. One end of each polyethylene tube can be attached to an adapter through a threaded fitting at preselected depths (for example, at 1.0 meter, at 5 meters and at depths larger than 5 meters). A gas sampling probe can be inserted into the gas conducting tubing between the upper end of the driving shaft and the vacuum/volume pump. A sample volume (for example, a few nano-grams) can be passively absorbed by the gas sampling probe during a particular time interval (for example, 14-17 days). The survey is considered completed at the end of the time interval. After the survey is completed, the gas sampling probes are removed from the installation locations and the gas sampling probes can be sent to a laboratory for analysis. The laboratory analysis can include extraction and identification of multiple types of hydrocarbons (C2-C20) adsorbed by each of the gas sensors. The results of the analysis can be stored in a database in association with the location of each gas sensor in the survey space. In some implementations, methane (C1) is not measured due to the fact that it can be generated from a biogenic source as well as a thermogenic source. The atmospheric gas can be removed from each gas sampling probe via a vacuum/volume pump and it can be discarded to the atmosphere. In some implementations, light hydrocarbons, such as ethane, propane, butane, pentane, hexane, other hydrocarbons and their isomers, helium and other rare earth gases that may be present in the soil gas sample, can be "filtered" out of the soil gas or trapped in various packings that are contained in the gas sampling probes (for example, concentrating device 120 illustrated in FIG. 1). The gas probes can collect up to 100 gas compounds (including aromatic and non-aromatic hydrocarbons).

At 204, the samples collected in each gas sampling probes are analyzed to identify the presence and the concentration of gas compounds of interest relative to their corresponding location in the surveyed volume. A portion of the collected gas compounds can be used to determine the hydrocarbon seepage. In some implementations, the analysis of gas compounds includes the identification of hydrocarbons in the range C2-C20, their polar compounds and their relations to non-polar compounds. The geochemical data associated with the location each gas sampling probe can be combined based on the spatial coordinates for generating a three-dimensional spatial distribution of the geochemical properties in the investigated locations and depths. In some implementations, the geochemical data are processed to reduce the noise or contaminant by filtering particular seepage-sensitive parameters. For example, filtering is done geostatistically by collecting background noise collected at control points known to be barren from petroleum accumulations or leaks, like dry holes. The geochemical data can include seepage-induced magnetic anomalies associated with oil and gas fields, which can be integrated with other geologic information to select a drilling location for the well that takes into account the structural characteristics (depth, width, and location) of the anomaly.

In some implementations, the seepage signature measured from a known accumulation having a defined geochemical signature can be compared to other seepage signatures measured at multiple selected depth intervals to increase the accuracy of seepage identification. For example, over a known hydrocarbon accumulation the composition of the gas is quantified and compared to that of the seepage obtained from multiple depths. Similar compounds can be attributed to the referenced accumulation and other compounds can be from non-targeted accumulations or noise. The accumulated compounds can be tested and verified over a known field. The signatures gathered from multiple depths versus a reference depth (for example, a location with known hydrocarbon accumulation can be cross-checked to subtract any noise or contaminant-related signals in order to match the most resembled signature to the actual one). The impact of contaminants or noise at the surface decreases with depth. True gas seepage can be distinguished from false readings based on the variation of hydrocarbon accumulation, which is approximately invariant or increases with depth. Performing a statistical analysis of the gas compounds, collected at multiple locations and depths, by combining multi-depth data can strengthen similarities (for example, increase significance of correlations) related to primary data and reduce noise.

At 206, the geochemical survey is repeated at different time intervals (for example, weeks or months apart) to investigate the hydrocarbon seepage variation over time and to generate a four-dimensional map of hydrocarbon microseepage. The statistical analysis of the gas compounds including the multi-depth comparison can be repeated at different times to identify which compounds are consistently measured and which of the measured compounds can be attributed to noise. The four-dimensional map of hydrocarbon microseepage can include complex patterns that indicate a source (for example, geographical coordinates of a hydrocarbon reservoir) and a trend of the hydrocarbon seepage. At 208, the seepage of hydrocarbons is determined based on processing the four-dimensional map of hydrocarbon microseepage. In some implementations, the four-dimensional map of hydrocarbon microseepage can indicate the spatio-temporal variation in seepage intensity in producing areas. At 210, the variation in intensity can be used to identify the pressure of identified hydrocarbon reservoirs. For example, significantly increasing seepage intensity can indicate overpressured reservoirs and low seepage intensity can indicate underpressured reservoirs.

The four-dimensional map of hydrocarbon microseepage can indicate the variation in concentrations of hydrocarbons in producing areas. The variation in concentrations of hydrocarbons can be used to identify active, passive, and fresh seepage. For example, active seepage leads to higher concentrations of hydrocarbons to the surface that can be detected based on the four-dimensional geochemical surveys. Fresh seepages can be associated with an active generation and migration system induced by faulting/fracturing and subsequent leakage from an old accumulation. Passive seepage can be detected based on the four-dimensional geochemical surveys that indicate a non-generating basin, resulting in weaker geochemical expressions at the surface, except in areas where major conduits are present such as faults. In some implementations, the geochemical expression at the surface can be used to identify the type of accumulation (for example, oil versus gas).

In some implementations, the method for detection of hydrocarbon seepage can utilize a combination of satellite, airborne, acoustic and seismic techniques along with underwater sensors to characterize and map hydrocarbons in a variety of environments. The combination of geophysical techniques along with multiple sensors provides a more complete characterization and mapping of hydrocarbons at basin scale exploration areas. The various independent technologies may include remote sensing (for example, satellite and/or airborne), seismic and acoustic imaging (for example, ship-based initially: multibeam echosounder, side-scan sonar, sub-bottom profiler; which may also be included in autonomous underwater vehicles (AUV) for unsurpassed imaging due to proximity to seafloor, but much more local in scope), magnetic and gravity surveying (either from ship or air-based tools, or from AUV more locally), chemical sensing (AUV: primarily mass spectrometer and fluorometer), and sediment, biological and chemical sampling (for example, piston cores typically, but may preferably utilize an underwater vehicle to obtain sediment, fluid (oil, water), or and/or gas samples for noble gases and isotope logs, and biology). The method may utilize airborne vehicles, ground vehicles, and marine vessels (for example, ships and/or underwater vehicles (for example, unmanned underwater vehicles, which may include remotely operated vehicles (ROVs) or AUVs). When combined into an integrated method, these technologies may determine the presence and location of thermogenic hydrocarbon seepages with complex patterns.

In some implementations, the method for detection of hydrocarbon seepage can also include chemical sensing. The detection of thermogenic hydrocarbons emanating from subterranean seeps, either at macro- or micro-scale may be detected to confirm whether hydrocarbon seeps are present at identified locations. Measuring concentrations of thermogenic methane, ethane, propane, butane, etc., near the seafloor can be performed via compact high-sensitivity mass spectrometers and laser fluorometers (for aromatic compounds generally associated with hydrocarbon liquids). The seep vent location provides a favorable site for additional biological and chemical sampling of fluids, gases, and sediments to further enhance the analysis. In particular, this method may include determining the presence and estimating information, such as depth, type, quality, volume and location, about a subsurface hydrocarbon accumulation from the measured data from the underwater vehicle. In particular, the present techniques involve the use of three independent technologies: clumped isotope geochemistry, noble gas geochemistry, and microbiology, which are combined and integrated as a workflow to enhance hydrocarbon exploration success. The use of three independent technologies may provide information about the depth, fluid type (oil versus gas) and quality, and volume of subsurface hydrocarbon accumulations to be determined from the sampling and analysis of the four-dimensional map of hydrocarbon microseepage combined with the ancillary information. That is, the hydrocarbon seepage detection method can integrate a plurality of biological, geochemical, and seismic indicators, such as structural position and reservoir, seal, or trap configuration to enhance the accuracy of seepage identification. At 212, the seepage identification can be used to initiate drilling in a hydrocarbon reservoir.

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus.

To provide for interaction with a user, implementations of the subject matter described in this specification can be implemented on any type of computer having a display device, for displaying information to the user and a keyboard and a pointing device, for example, a mouse or a trackball, by which the user can provide input to the computer. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input.

While this specification contains many specific implementation details, these should not be construed as limitations on the scope of any inventions or of what can be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features can be described above as acting in certain combinations and even initially claimed as such, one or more features from a claimed combination can in some cases be excised from the combination, and the claimed combination can be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing can be advantageous.

What is claimed is:

1. A method of sampling a geographic region for hydrocarbon seepage, the method comprising:
    detecting, by a first hydrocarbon sensor, hydrocarbon seepage at a first sampling depth from a surface in a surveyed geographic region;
    detecting, by a second hydrocarbon sensor, hydrocarbon seepage at a second sampling depth from the surface, the second sampling depth deeper than the first sampling depth;
    detecting, by a third hydrocarbon sensor, hydrocarbon seepage at a third sampling depth from the surface, the third sampling depth deeper than the second sampling depth;
    comparing, by a processor, each of the hydrocarbon seepage at the first sampling depth, the hydrocarbon seepage at the second sampling depth, and the hydrocarbon seepage at the third sampling depth with hydrocarbon seepage at a reference depth deeper than the first, second and third sampling depths, wherein hydrocarbon seepage at the reference depth is known; and
    determining, by the processor, hydrocarbon seepage through the surveyed geographic region based on a result of comparing each of the hydrocarbon seepage at the first sampling depth, the hydrocarbon seepage at the second sampling depth, and the hydrocarbon seepage at the third sampling depth with the hydrocarbon seepage at the reference depth.

2. The method of claim 1, wherein the first sampling depth is about 1.0 meter from the surface.

3. The method of claim 1, wherein the second sampling depth is about 5.0 meter from the surface.

4. The method of claim 1, wherein the third sampling depth is greater than 10.0 meters from the surface.

5. The method of claim 1, further comprising analyzing, based on the hydrocarbon seepage the first sampling depth, the hydrocarbon seepage at the second sampling depth, and the hydrocarbon seepage at the third sampling depth, a relationship between polar compounds and non-polar compounds included in the hydrocarbon.

6. The method of claim 1, further comprising initiating drilling at a location in the surveyed geographic region, the location selected based on the determined hydrocarbon seepage through the surveyed geographic region.

7. The method of claim 1, wherein the hydrocarbon seepage at the first sampling depth, the hydrocarbon seepage at the second sampling depth and the hydrocarbon seepage at the third sampling depth are detected at a first time instant, and wherein the method further comprises:
    detecting, at a second time instant after the first time instant, hydrocarbon seepage at the first sampling depth;
    detecting, at the second time instant, hydrocarbon seepage at a second sampling depth from the surface, the second sampling depth deeper than the first sampling depth;
    detecting, at the second time instant, hydrocarbon seepage at a third sampling depth from the surface, the third sampling depth deeper than the second sampling depth; and
    comparing, by the processor, each of the hydrocarbon seepage at the first sampling depth detected at the second time instant, the hydrocarbon seepage at the second sampling depth detected at the second time instant, and the hydrocarbon seepage at the third sampling depth detected at the second time instant with hydrocarbon seepage at the reference depth determined at the second time instant.

8. The method of claim 7, further comprising determining hydrocarbon seepage through the surveyed geographic region as a function of time based on a result of the comparing at the first time instant and the comparing at the second time instant.

9. The method of claim 1, wherein detecting hydrocarbon seepage at the first sampling depth comprises, detecting hydrocarbon seepage at the second sampling depth and detecting hydrocarbon seepage at the third sampling depth comprises:

positioning a first plurality of hydrocarbon sensors at the first sampling depth;

positioning a second plurality of hydrocarbon sensors at the second sampling depth; and positioning a third plurality of hydrocarbon sensors at the third sampling depth, wherein the first plurality of hydrocarbon sensors, the second plurality of hydrocarbon sensors and the third plurality of hydrocarbon sensors are configured to detect hydrocarbons at the first sampling depth, the second sampling depth and the third sampling depth, respectively.

10. The method of claim 9, wherein positioning the first plurality of hydrocarbon sensors at the first sampling depth comprises positioning the first plurality of hydrocarbon sensors in a two-dimensional array at the first sampling depth.

11. The method of claim 9, wherein positioning the second plurality of hydrocarbon sensors at the second sampling depth comprises positioning the second plurality of hydrocarbon sensors in a two-dimensional array at the second sampling depth.

12. The method of claim 9, wherein positioning the third plurality of hydrocarbon sensors at the third sampling depth comprises positioning the third plurality of hydrocarbon sensors in a two-dimensional array at the third sampling depth.

13. The method of claim 1, further comprising positioning a reference hydrocarbon sensor at the reference depth, the reference hydrocarbon sensor configured to detect hydrocarbons at the reference depth.

14. The method of claim 13, wherein the reference depth is within a hydrocarbon reservoir in the surveyed geographic region.

15. The method of claim 13, wherein comparing each of the hydrocarbon seepage at the first sampling depth, the hydrocarbon seepage at the second sampling depth, and the hydrocarbon seepage at the third sampling depth with hydrocarbon seepage at a reference depth deeper than the first, second and third sampling depths comprises detecting hydrocarbon seepage at the reference depth.

16. The method of claim 13, wherein comparing each of the hydrocarbon seepage at the first sampling depth, the hydrocarbon seepage at the second sampling depth, and the hydrocarbon seepage at the third sampling depth with hydrocarbon seepage at a reference depth deeper than the first, second and third sampling depths comprises:

determining, by the processor, a reference hydrocarbon seepage signal that represents the hydrocarbon seepage at the reference depth;

determining, by the processor, a first hydrocarbon seepage signal that represents the hydrocarbon seepage at the first sampling depth;

determining, by the processor, a second hydrocarbon seepage signal that represents the hydrocarbon seepage at the second sampling depth;

determining, by the processor, a third hydrocarbon seepage signal that represents the hydrocarbon seepage at the third sampling depth;

subtracting, by the processor, the first hydrocarbon seepage signal from the reference hydrocarbon seepage signal;

subtracting, by the processor, the second hydrocarbon seepage signal from the reference hydrocarbon seepage signal; and subtracting, by the processor, the third hydrocarbon seepage signal from the reference hydrocarbon seepage signal.

* * * * *